United States Patent [19]

Buehler et al.

[11] 4,311,690

[45] Jan. 19, 1982

[54] TEST SET AND METHOD FOR THE DETERMINATION OF FREE HORMONES

[75] Inventors: Robert J. Buehler, Holliston; Teresa H. Chan, Burlington, both of Mass.; Franklin Lim, Richmond, Va.

[73] Assignee: Damon Corporation, Needham Heights, Mass.

[21] Appl. No.: 48,628

[22] Filed: Jun. 14, 1979

Related U.S. Application Data

[63] Continuation-in-part of Ser. No. 917,365, Jun. 20, 1978, abandoned.

[51] Int. Cl.$^3$ ............... G01N 33/56; A61K 43/00; B01J 13/02
[52] U.S. Cl. ............................ 424/1; 23/230 B; 424/12; 252/316
[58] Field of Search ............... 424/1, 12; 23/230 B; 252/316

[56] References Cited

U.S. PATENT DOCUMENTS

| | | | |
|---|---|---|---|
| 3,716,632 | 2/1973 | Fader et al. | 424/1 |
| 3,730,684 | 5/1973 | Demetriou | 23/230 B |
| 3,816,076 | 6/1974 | Backer | 23/230 B |
| 3,850,577 | 11/1974 | Ashkar | 23/230 B |
| 3,911,096 | 10/1975 | Chopra | 424/1 |
| 3,928,553 | 12/1975 | Hollander | 424/1 |
| 3,929,981 | 12/1975 | Murty et al. | 424/1 |
| 3,941,564 | 3/1976 | Fader et al. | 23/230 B |
| 3,947,564 | 3/1976 | Shannon et al. | 424/1 |
| 4,066,410 | 1/1978 | Eisentraut | 23/230.6 |

OTHER PUBLICATIONS

Biomedical Applications of Immobilized Enzymes and Proteins, C. F. Thomas, M. S. Chang, Plenum Press, 1977.
Free T-4, $^{125}$I Radioimmunoassay Test System, Corning Medical, Dec. 1977.
Bueler et al., Clin. Chem., vol. 24, No. 6, Jun. 1978, p. 1040.

*Primary Examiner*—Christine M. Nucker

[57] ABSTRACT

Disclosed is a process for determining the concentration of unbound hormone, e.g., thyroxine, cortisol, or testosterone, in a liquid sample containing hormone and protein capable of binding the hormone. The sample is incubated with antibody specific to the hormone to be detected and a distinguishable analogue of the hormone, both of which are separated from the sample by semipermeable membranes capable of excluding the passage of natural protein and antibody but which allow passage of the hormone and its analogue. Preferably, the antibody and analogue are contained in semipermeable microcapsules. Free hormone in the sample permeates the membranes and competes for sites of attachment to the antibody with the analogue. The antibody and free hormones are then separated. The amount of analogue present either in association with the antibody or in the remainder of the reaction system is indicative of the level of free hormone originally present in the sample.

12 Claims, 6 Drawing Figures

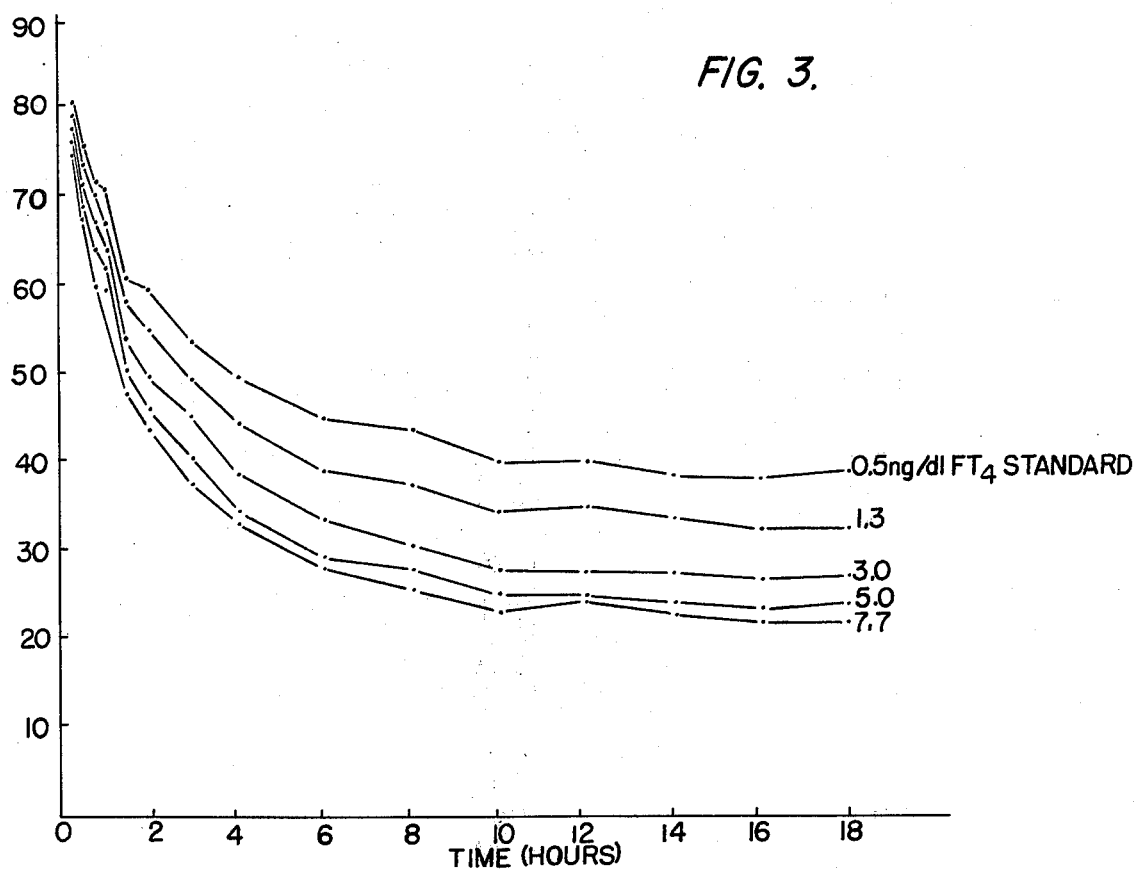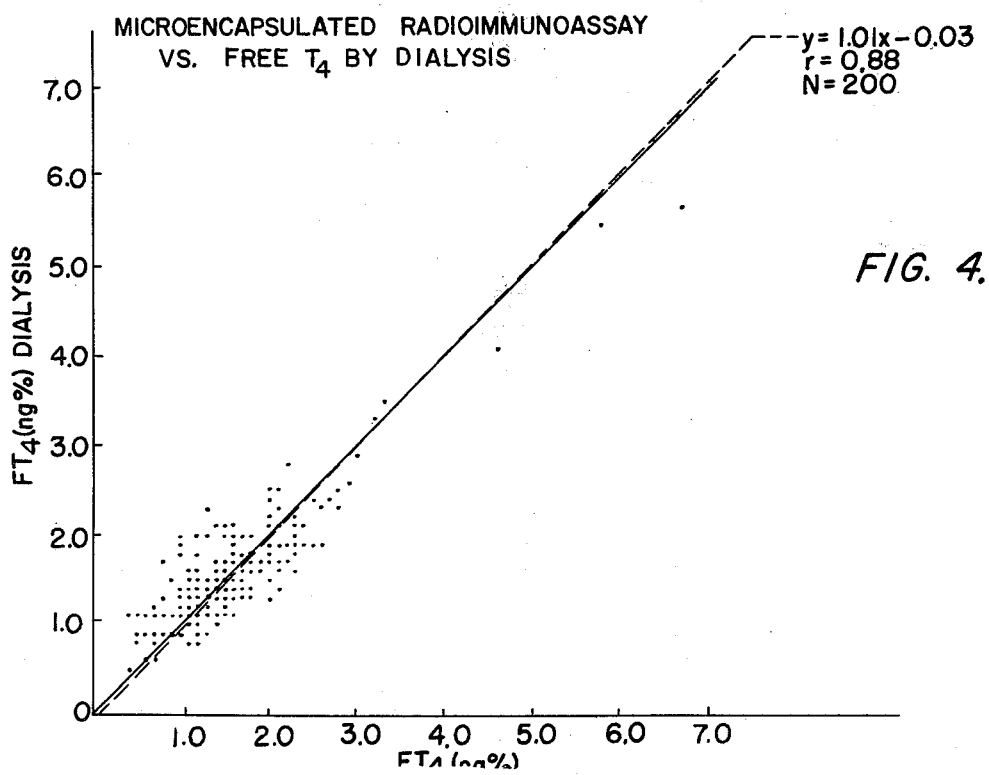

TEST SET AND METHOD FOR THE DETERMINATION OF FREE HORMONES

REFERENCE TO RELATED APPLICATION

This application is a continuation-in-part of application Ser. No. 917,365, filed June 20, 1978, now abandoned.

BACKGROUND OF THE INVENTION

This invention relates to the detection of the presence and concentration of unbound species, e.g., hormones, in a liquid sample such as serum. More particularly, it relates to the detection of free species of the type which are capable of reversibly binding with protein in samples containing the free species, the binding protein, and a concentration of species-protein complex.

The "competitive assay" technique for measuring the concentration of various biologically active substances for diagnostic purposes is now well established. The technique involves a reaction system wherein antibody specific to the species to be determined is incubated together with the test sample and an aliquot of a distinguishable analogue of the sample. The analogue and natural species compete for sites of attachment to the antibody, and after separation of the antibody from the remainder of the reaction system, the antibody or supernatant may be assayed for analogue. The amount of analogue associated with the antibody is an inverse function of the concentration of the test species in the sample.

Hormones such as those excreted from the thyroid, tests, ovaries, adrenal cortex, and other mammalian glands are often transported through the circulatory system in association with hormone binding proteins or globulins. Often, it is of diagnostic significance to be able to determine the presence and concentration of free hormone, as opposed to protein-bound hormone or total hormone. For example, thyroxine ($T_4$) in the bloodstream exists in a dynamic equilibrium as a species bound to a transport protein, (thyroxine-binding globulin, albumin, or pre-albumin) and, in a small fraction (potentially 0.1% or less), as an unbound substance ("free" or unbound $T_4$). Free $T_4$ is thought to be the active species of the thyroid hormone system. Unfortunately, free-$T_4$ assay methodology has been tedious, complicated, expensive, and error-prone because of the difficulty in standardization of materials and in measuring minute quantities of unbound hormone in the presence of overwhelming amounts of hormone relatively loosely bound to protein. The competitive assay procedure noted above is not capable of determining free species concentrations.

Of the methods for measuring free $T_4$ and other hormones which exist in vivo as protein complexes, the dialysis method affords a high degree of accuracy. A dialysis bag containing known quantities of serum to be tested and labled hormone is suspended in buffer. The labled hormone distributes itself between the free and bound states in the same proportions as the serum hormone. The mass of labled hormone added must be extremely small so as to avoid seriously perturbing the system, yet the count rate must be high so that detection of small amounts is feasible. In the case of radioactive lables, this requires that labled hormone of very high specific activity be used. After a suitable period (about 24 hours), the tagged and natural hormone not bound to protein diffuse through the semipermeable dialysis bag while hormone bound to protein (molecular weight greater than 20,000) remains within the dialysis bag. To determine the quantity of free hormone present in the serum, one assays an aliquot of the buffer for labled hormone. As a result of the assay, the fraction of labled hormone that crossed into the buffer may be calculated, and the fraction of total hormone that exists in the free state inferred. To convert this fraction to mass units (e.g., ng/dl) of free hormone, a total hormone assay must also be run on the sample.

While this system can give meaningful results in free $T_4$ and other free hormone assays, it is poorly suited for routine use. Two tests must be run, and the accuracy of the final result can be compromised by either procedure. Rather large amounts of radioactivity must be employed per test. Interfering impurities in the labeled hormone can cause special problems, and long incubation times are required. Only serum can be used, and it must be extremely fresh. Furthermore, the collection and standardization of all the materials necessary for the assay is not a routine matter. Thus, the application of the procedure has been limited due to the high cost and labor intensity of the method and the skilled personnel required.

Another method of free hormone assay involves reaction kinetics and requires two separate tests. Each test measures a kinetic curve related to how fast an antibody captures hormone, e.g., $T_4$, away from the opposing pull of the primary binder such as thyroxine binding globulin.

In such an assay system, inaccuracies result from several pathologic conditions. If more protein binding sites are present than usual, the effective attraction of the globulin for the hormone will be greater and the rate of binding to antibody will decrease. In the case of thyroxine analysis, this would give the appearance that the sample had little $T_4$ when in fact there might be a high level of $T_4$, but all bound.

SUMMARY OF THE INVENTION

The instant invention provides a process, reagent, and test set for the direct assay of unbound hormones and other such species. The assay may be performed in the presence of the subject serum proteins and the bound hormone.

In accordance with the invention, semipermeable microcapsules containing antibody complementary to the hormone or other species to be detected are incubated with both a distinguishable analogue of the hormone and the test sample. Preferably, the analogue is introduced into the microcapsules prior to the incubation in quantities such that the antibody is saturated at the hormone binding sites. The microcapsule walls comprise membranes separating the test sample from the antibody, and have a permeability sufficient to allow passage of free species and its analogue, but insufficient to permit passage of the antibody, natural proteins, or protein-bound hormone. When a test sample is added to an aliquot of the microcapsules, free hormone diffuses through the membranes and competes with its analoque for sites of attachment on the antibody. Thus, the distribution of analogue between the antibody and the remainder of the reaction system becomes indicative of the amount of free hormone originally present in the sample.

Next, the antibody together with its bound hormone (and bound analogue) is separated from the free species, and either the antibody or the remainder of the reaction system is assayed for analogue. The separation may be conducted by conventional centrifugation procedures or by inducing an osmotic change so that the capsules collapse and unbound hormones migrate out of the capsules. This can be accomplished, for example, by adding serum albumin or polyethyleneimine to the system which promotes efflux of intracapsular liquid. Results are interpreted by comparing the assay of analogue content to a standard, such as a curve of free hormone concentration vs. radioactive count, fluorescent intensity, or other marker characteristic used to indicate the presence of the analogue.

The assay may be used to detect the presence and/or concentration of free thyroxine, tri-iodothyronine, neonatal thyroxine, testosterone, cortisol, other steroid hormones, and other substances which reversibly bind with protein. Essentially any such material may be determined provided a complementary binding substance and a distinguishable analogue of the material is available or can be produced.

The assay may be routinely conducted using a test set sold as a mercantile unit comprising microcapsules containing antibody and analogue, standards and blanks containing predetermined concentrations of the subject species, and a reagent for scavenging unbound hormone and analogue from the capsules after completion of the incubation.

Objects of the invention are to provide a rapid, simple, and reproducible method of detecting the presence and concentration of species unbound to protein in a liquid sample, a reagent useful in such assays, and a test set suitable for rapidly and conveniently conducting such assays. Another object is to provide a method of determining free $T_4$ is samples extracted from human blood and containing protein bound $T_4$. These and other objects and features of the invention will be apparent from the description which follows.

BRIEF DESCRIPTION OF THE DRAWINGS

FIG. 3 is a graph of cpm from $T_4$ ($^{125}I$) bound to $T_4$ antibody contained within semipermeable microcapsules immersed in standard solutions of free $T_4$ vs. time. As serum $T_4$ replaces $T_4$ ($^{125}I$) at $T_4$ antibody binding sites, the cpm remaining in association with the antibody decreases. Note that the rate of replacement is largely linear to two hours of incubation at 37° C.;

FIG. 4 graphically illustrates the correlation of results between the dialysis assay technique and the microencapsulation system of the invention;

DESCRIPTION OF THE PREFERRED EMBODIMENT

Figure 1:
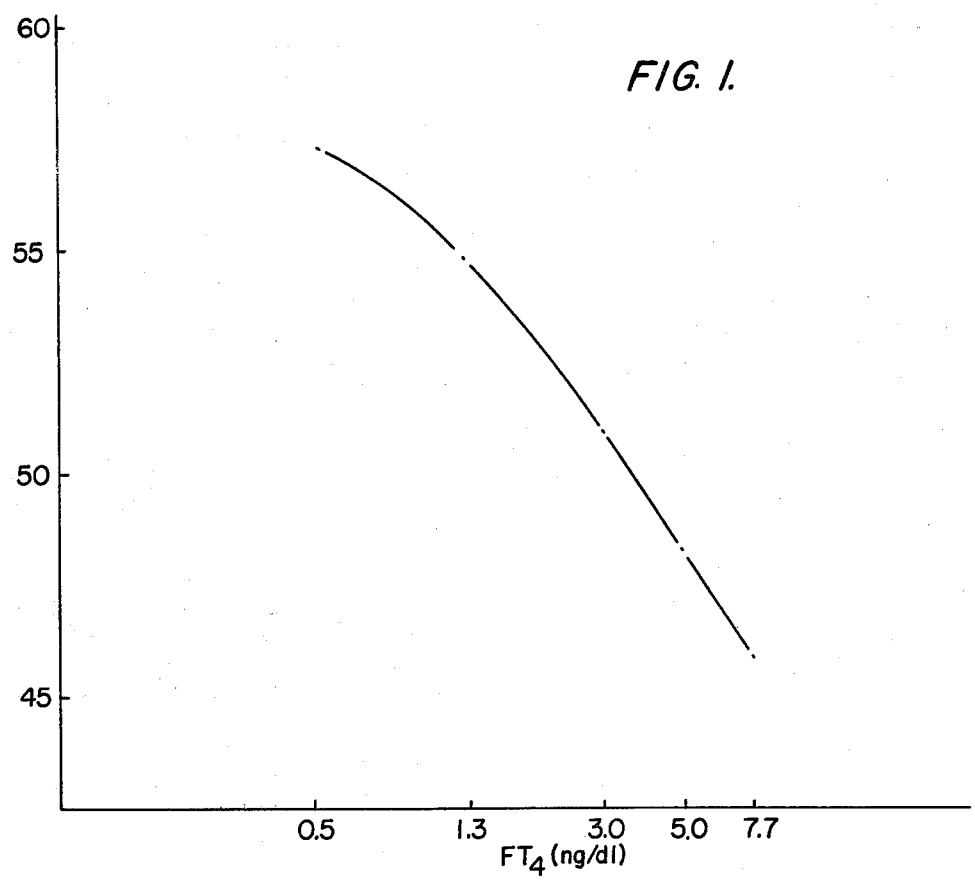
FIG. 1 illustrates a standard curve made in accordance with the procedure of the invention. It consists of a plot of counts per minute ($\times 10^3$) on a y-axis linear scale vs. free-$T_4$ concentration in ng/dl on an x-axis log scale (see Table 1 for data)

The process of the invention requires that the sample containing the species to be detected be incubated with antibody complementary to the species (or other substance capable of reversibly binding with the species) and a distinguishable analogue of the species, and that the sample and antibody be separated by a semipermeable membrane or membranes that exclude the passage of high molecular weight proteins.

Antibodies to selected hormones may be produced in accordance with well-known techniques involving injection of the hormone into laboratory animals, possibly together with an adjuvant, and subsequently extracting and purifying the produced antibodies. Many such antibodies are available commercially. Many distinguishable analogues of species detectable by the process of the invention are also commercially available or can be made using known techniques. The term "distinguishable analogue" as used herein, refers to a molecule which has antibody binding properties similar to and preferably identical to the species sought to be detected, and which is characterized by a property which allows a measure of its concentration to be readily obtained. Preferred analogues comprise a sample of the species to be detected tagged with a radioactive atom: for example, thyroid hormones may be conveniently tagged with $^{125}I$ and can then be quantitated by measuring gamma radiation. However, it is contemplated that other types of analogs may be employed, so long as the analogue has a molecular weight and resulting dimensions well below those of natural proteins and the antibody used. Thus, analogues may be produced by tagging a sample of the species to be detected with a relatively low molecular weight enzyme, fluorescent moiety, or other moiety which enables quantitative measurement of the concentration of the analogue by physical or chemical means.

To practice the assay, the antibody and analogue must be separated from the sample by one or more membranes having a permeability sufficient to preclude the passage of antibodies and natural proteins (which uniformly have a molecular weight in excess of 20,000 daltons) but sufficient to allow free passage of the species to be detected and its analogue. In a preferred embodiment of the invention, the membranes take the form of semipermeable microcapsules containing the antibody and analogue.

It is noteworthy that the semipermeable microcapsules used have a permeability similar to the dialysis membranes described above. However, the semipermeable microcapsule wall is hundreds of times thinner than conventional dialysis membranes, and its available surface area is orders of magnitude larger per unit weight. Free-$T_4$ or other free hormones freely enter the microcapsule and displaces, in proportion to its concentration, labled $T_4$ from the $T_4$ antibody. Thus, an equilibrium of free $T_4$ and labeled $T_4$ is approached within the capsule during the incubation period.

Suitable methods of encapsulating biological materials in membranes having the foregoing permeability properties are disclosed in detail in U.S. patent application Ser. Nos. 606,166, (Aug. 20, 1975), 931,177 (Aug. 4, 1978), and 30,847 (Apr. 17, 1979), all to F. Lim et al., and in U.S. application Ser. No. 24,600 (March 28, 1979) to F. Lim. The presently preferred method of producing such microcapsules produces semipermeable polyamide membranes by an interfacial polycondensation technique. Mutually immiscible solvents or solvent systems are selected. e.g, water and a cyclohexane based solvent, and one monomer of a complementary pair which form a copolymer is dissolved in the water together with the material to be encapsulated. The aqueous solvent containing the material to be encapsulated is then emulsified within the other solvent to form a plurality of discrete droplets. The second, complementary monomer is next added to the continuous phase of the emulsion to initiate polymerization about the droplets at the phase boundary. Membrane permeability and uniformity of polymer depositions are controlled by varying the affinity of the continuous phase of the emulsion for the encapsulated monomer during the course of polymerization and by controlling the concentration of the reacting monomers and the duration of the polymerization.

In one approach, the continuous phase at the outset is a solvent or solvent system having a relatively high affinity for the encapsulated monomer so that, in a first stage of polymerization, a relatively thick polymer network is produced about the droplets. Thereafter, the continuous phase is altered such that its affinity for the first monomer is decreased, e.g., by diluting the continuous phase with a second solvent or by replacing the continuous phase with a fresh solvent. Upon the addition of second monomer, further polymerization occurs preferentially within the initially deposited polymer network, patching macroporous defects and resulting in uniform capsule membranes which allow diffusion of solutes below a certain molecular weight.

In another approach, the continuous phase at the outset is selected to have a low affinity for the encapsulated monomer so that thin, relatively dense membranes form in a first stage of polymerization. Thereafter, the affinity of the continuous phase for the encapsulated monomer is increased to draw further quantities of monomer through the membrane and to deposit a second outer layer of insoluble polymer.

When the discontinuous aqueous droplet phase is buffered to provide a compatible environment for labile biological materials such as an antibody, the encapsulation can be conducted in a manner to preserve a large percentage of the labile material's biological activity. The operability of the encapsulated material is also preserved by adding second monomer to the continuous phase in increments over the duration of the polymerization so that is concentration at any given time is relatively low and the antibody is not exposed to high concentrations of potentially destructive substances.

In a preferred reaction system, aqueous droplets containing a diamine, a high molecular weight filler material, and the antibody are produced in a continuous phase of cyclohexane whose affinity for the monomer dissolved in the droplet phase is modified by the addition of chloroform as a diluent. The addition of a diacid halide to the system results in the formation of semipermeable polyamide microcapsules. This microencapsulation approach is effective for producing membranes having an upper limit of permeability in the 2000–30,000 dalton molecular weight range. Thus, the capsules can easily be engineered to permit the diffusion of many hormones.

To conduct the assay, the test sample is mixed with microcapsules of the type described and incubated, preferably at about 37° C. for about two hours. Preferably, prior to the incubation the capsules are suspended in a solution of the hormone analogue of sufficient concentration to load the antibody with a detectably amount of the analogue concentration. However, the assay can be conducted by adding the analogue to the reaction system during or after the incubation with serum. Protein in the sample and protein-species complexes cannot traverse the microcapsule wall.

Next, the antibody is separated from the remainder of the reaction system (optionally exclusive of the microcapsule membranes) and either the antibody or the remainder of the system is assayed for analogue. In the preferred method of making the separation, a high molecular weight hydrophilic material such as a solution of polyethylenimine or serum albumin is added to the extracapsular volume. This induces an osmolality increase resulting in collapse of the microcapsules and migration of intracapsular unbound hormone and its analogue into the supernatent. The result is a packed pellet of encapsulated antibody which, after an optional centrifuge treatment, may be isolated by aspirating or decanting the supernatent.

Figure 2:
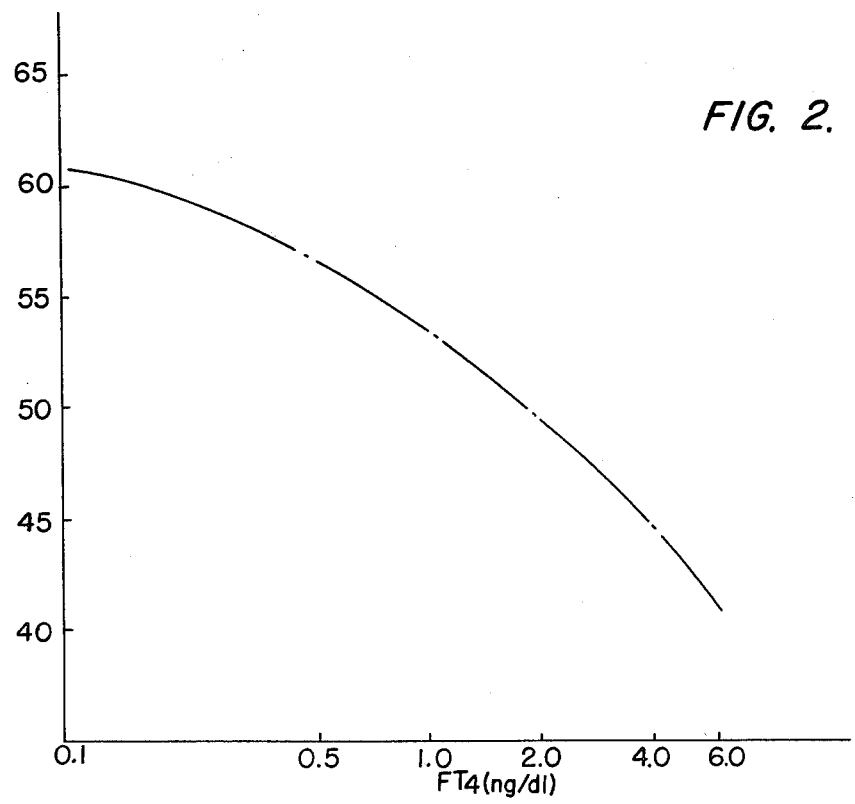
FIG. 2 illustrates a second standard curve for a free $T_4$ assay of the invention in cpm (linear) v. ng/dl free-$T_4$ (log scale). Data for this figure is found in Table 2.

Tables 1 and 2, and corresponding FIGS. 1 and 2 of the drawing disclose the results of assays embodying the invention designed to detect the presence of free $T_4$ using free $T_4$ antibody, $^{125}I$ labled thyroxine as an analogue, and solutions of known free $T_4$ concentration. Tests of unknowns run in parallel with the procedure used to gather this data may be interpreted by reference to the standard curves.

TABLE 1

| Free $T_4$ Assay Standard Curve | | |
|---|---|---|
| Free $T_4$ | CPM | MEAN CPM |
| 0.5 ng/dl | 57097 | 57,285 |
|  | 57472 |  |
| 1.3 ng/dl | 54256 | 54,839 |
|  | 54717 |  |
| 3.0 ng/dl | 50960 | 50,953 |
|  | 50946 |  |
| 5.0 ng/dl | 48487 | 48,302 |
|  | 48117 |  |
| 7.7 ng/dl | 45982 | 46,025 |
|  | 46067 |  |
| TOTAL COUNT $T_4(^{125}I)$ ADDED incubation 2 hours, 37° C. | 86,403 | |

TABLE 2

| Free $T_4$ Assay Standard Curve | | |
|---|---|---|
|  |  | AVG. CPM |
| 0.1 ng/dl | 61219 |  |
|  | 60398 | 60933 |
|  | 61183 |  |
| 0.5 ng/dl | 58020 |  |
|  | 55618 | 56675 |
|  | 56389 |  |
| 1.0 ng/dl | 52096 |  |
|  | 52671 | 52824 |
|  | 53705 |  |
| 2.0 ng/dl | 48483 |  |
|  | 50126 | 49536 |
|  | 49971 |  |
| 4.0 ng/dl | 44853 |  |
|  | 45108 | 44732 |
|  | 44235 |  |
| 6.0 ng/dl | 42008 |  |
|  | 41344 | 41456 |
|  | 41015 |  |
| TOTAL COUNT $T_4 (^{125}I)$ ADDED 2 hour incubation, 37°C. | 86,903 | |

The invention will be further understood from the following, non limiting example.

Preparation of Microcapsules

Hexanediamine carbonate (pH=8.5±0.1) solution is prepared by mixing 17.7 ml 1,6 hexanediamine with 32 ml of water, and bubbling $CO_2$ through the solution for about 1 hour or until the pH level is reached. Terephthaloyl chloride (TCl) solution is prepared by adding 20 g TCl in 200 ml of organic solvent consisting of 4 parts cyclohexane and 1 part chloroform. TCl is dissolved by stirring vigorously, and the solution is then centrifuged for 10 minutes at 2600 rpm. Any precipitate is discarded.

750 ml cyclohexane are mixed with 125 ml SPAN-85 (emulsifier, fatty acid ester or sorbitan) in a 2-liter mixer equipped with a magnetic stirring bar. While stirring, a mixed solution made from one ml antiserum to thyroxine (4% in phosphate buffered saline, R. F. Laboratories, Houston, Texas, or Radioassay Systems Laboratories, Carson, Cal.), 25 ml of polyvinyl pyrrolidone—4% bovine serum albumin, and 30 ml of hexanediamine carbonate solution is added to the cyclohexane. When droplets of the desired size have been produced, 70 ml TCl solution are added. Thirty seconds later, 37.5 ml of TCl are added. Sixty seconds later, 25 ml of chloroform are added. Three additional 25 ml aliquots of chloroform are added at 30 second intervals.

The microcapsules are recovered by centrifuging the two-phase reaction system, decanting the supernatant, and mixing the capsules with TWEEN-20 (polyoxyethylene derivative of fatty acid partial ester of sorbitol anhydride - emulsifier buffered with $NaHCO_3$) and phosphate buffered saline. The capsules retain the polyvinylpyrrolidone and bovine serum albumin filler materials, as well as the thyroxine antibody.

Saturation of Antibody with Analogue

Microcapsules made in accordance with the foregoing procedure may be loaded with $^{125}I$ labeled thyroxin (Cambridge Nuclear Corporation, Billerica, Massachusetts) by the following steps.

1. Add to each of 100 standard tubes 0.8 ml of microcapsul suspension and 0.1 microCurie of $T_4$ ($^{125}I$) (high specific activity of 5-6000 micro Ci per microgram). Allow to incubate at 37° C. for at least thirty (30) minutes.
2. Wash the microcapsules with twice their volume of phosphate buffered saline (0.15 M NaCl, pH=7.5, 0.015 M phosphate buffer).
3. Centrifuge at 2000 xg for 15 minutes and decant supernatant.
4. Repeat steps 2 and 3 twice.
5. Dilute microcapsule suspension with 1.6 times their volume of the phosphate buffered saline disclosed above. Total volume equals 80 ml. 0.8 ml of microcapsule suspension are used per test; thus, 100 tests may be conducted with the capsules.

Test Procedure (1) Place 25 microliter test samples and 5 samples of known free $T_4$ concentration in separate tubes. In the standard curve from Table 1, concentrations of 0.5, 1.3, 3.0, 5.0 and 7.7 ng% of free $T_4$ were used, but any series of free $T_4$ concentrations may be adapted according to well-known experimental techniques. A control tube containing 25 microliters of saline may also be included as a further check on assay accuracy.

(2) Pipette 800 microliter of $T_4$ ($^{125}I$) pre-saturated microcapsules (supplied as such) into each tube.

(3) Vortex each tube and incubate for 120 minutes at 37° C.

(4) After incubation, add 1.0 ml of 1.0% polyethyleneimine (m.w. 40-50 thousand) in phosphate buffered saline to each tube.

(5) Incubate for an additional 20 minutes.

(6) Decant supernatants.

(7) Count each tube for one minute in a gamma counter.

Calculation of Results (1) Each time an assay is run for determination of unknown free-$T_4$ concentration in a sample(s), standards to prepare the standard curve should be run.

(2) Upon completion of the assay, a standard curve such as shown in FIG. 1 or 2 is prepared using values obtained from the standards which were assayed concurrently with unknown samples.

(3) Counts per minute (cpm) for each value can be plotted in the linear scale of 2 cycle semilog graph paper versus free-$T_4$ concentration in nanogram percent of the log scale.

An alternative to plotting cpm v. free $T_4$ concentration is to plot percent bound (relative) v. free $T_4$ concentration. This can be accomplished by calculating the percent bound (relative) for each standard, control, or unknown and plotting these values on two cycle semilog paper in a manner similar to that described previously for cpm. Percent bound (relative) is calculated as follows: percent bound (relative)=cpm bound/means cpm bound of standard of lowest free $T_4$ concentration.

FIG. 4 is a graph of free $T_4$ concentration in ng% of about 200 test samples, each of which were assayed by the method of this invention and the dialysis method. As shown, there is a high degree of correlation between the two test methods.

Figure 5:
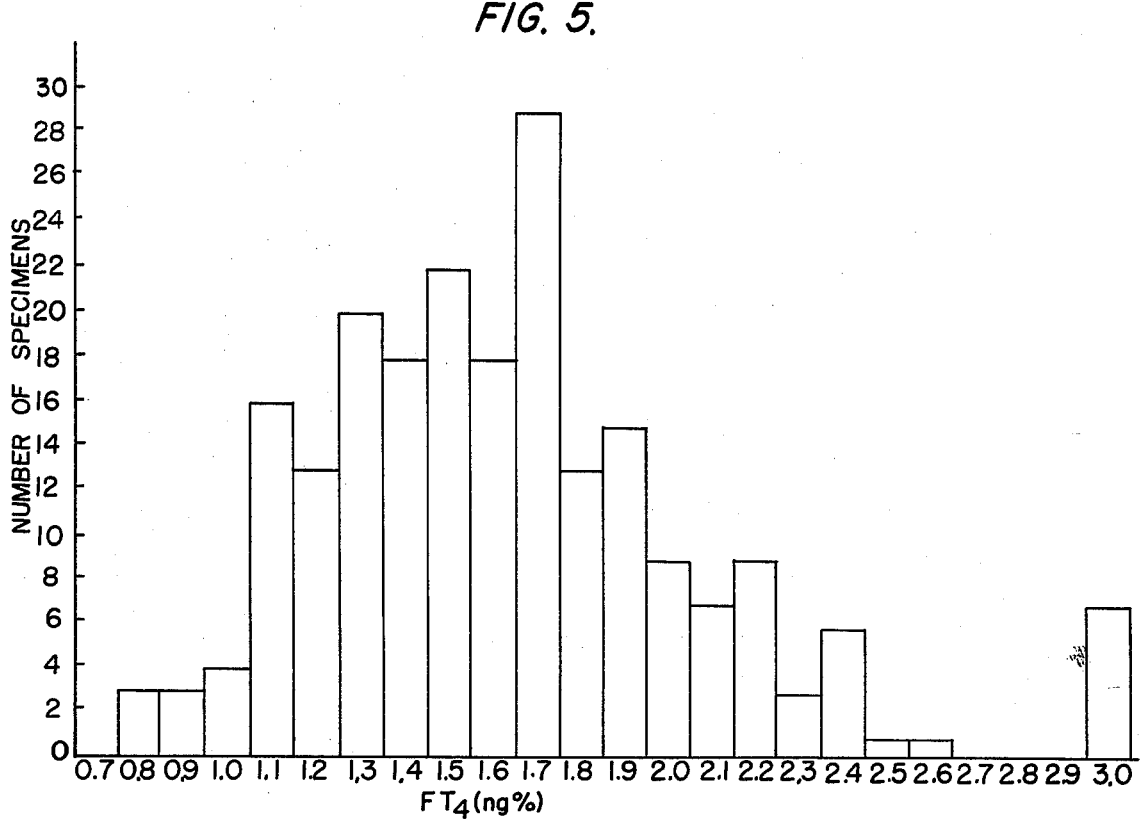
FIG. 5 graphically illustrates the normal range of free $T_4$ as established by the microencapsulated assay system.

FIG. 5 is a graph of frequency of a given free $T_4$ concentration vs. free $T_4$ concentration based on some 200 test samples assayed in accordance with the procedure set forth above.

Figure 6:
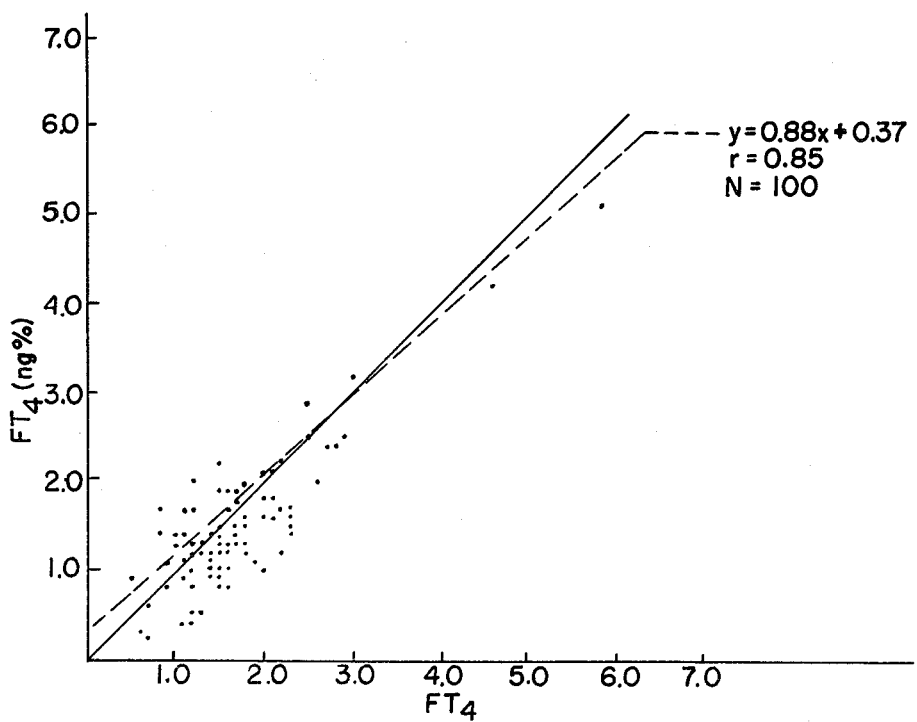
FIG. 6 graphically illustrates the correlation between kinetic radioimmunoassay and the microencapsulated type assay system of the invention.

FIG. 6 is a graph of free $T_4$ concentration in ng% of about 100 test samples, each of which were assayed by the method of this invention and the kinetic radioassay technique. As shown, there is a high degree of correlation between the two test methods.

Table 3 shows the consistency of the results intra assay.

TABLE 3

| Intra Assay Variation (Values in ng/dl) | | |
| --- | --- | --- |
| Level A (1.2) | Level B (2.0) | Level C (5.3) |
| 1.5 | 2.3 | 3.6 |
| 1.3 | 2.1 | 4.2 |
| 1.1 | 2.2 | 4.2 |
| 1.1 | 2.1 | 3.3 |
| 1.2 | 2.1 | 3.3 |
| 1.3 | 2.0 | 3.9 |
| 1.3 | 1.7 | 4.1 |
| 1.4 | 2.1 | 3.7 |
| 1.2 | 2.5 | 3.5 |
| 1.3 | 1.8 | 3.5 |
| 1.3 | 2.2 | 4.4 |
| 1.3 | 2.1 | 3.9 |
| 1.6 | 2.3 | 4.6 |
| 1.2 | 2.5 | 4.6 |
| 1.3 | 2.3 | 4.4 |
| 1.2 | 2.1 | 4.2 |
| 1.2 | 2.1 | 3.4 |
| 1.3 | 2.3 | 3.8 |

TABLE 3-continued

| | | |
|---|---|---|
| 1.5 | 2.1 | 4.2 |
| 1.4 | 2.2 | 4.6 |
| 1.4 | 2.1 | 3.7 |
| 1.4 | 2.1 | 4.0 |
| 1.4 | 2.1 | 4.0 |
| 1.4 | 2.3 | 4.3 |
| 1.4 | 2.3 | 4.0 |
| 1.6 | 2.4 | 4.0 |
| 1.3 | 2.0 | 4.2 |
| 1.2 | 2.1 | 4.2 |
| | 2.4 | 4.5 |

| Coefficient of Variation | Number x + S.D. | C.V. |
|---|---|---|
| A | 28 1.34 ± .13 | 9.6% |
| B | 29 2.2 ± .17 | 7.7% |
| C | 29 4.1 ± .38 | 9.3% |

Table 4 shows the consistency of results, interassay.

TABLE 4

| | Interassay Variation: (values in ng/dl) | | |
|---|---|---|---|
| Test # | Level A (1.2) | Level B (2.0) | Level C (5.3) |
| 1 | 1.3 | 2.4 | 4.6 |
| | 1.2 | 1.8 | 4.4 |
| 2 | 1.4 | 1.5 | 4.6 |
| | 1.5 | 2.6 | 4.7 |
| | 1.2 | 2.0 | 4.0 |
| | 1.3 | 2.0 | 3.7 |
| | 1.4 | 2.5 | 3.8 |
| | 1.2 | 1.9 | 4.0 |
| 3 | 1.3 | 2.2 | 3.9 |
| 4 | 1.4 | 2.0 | 3.2 |
| | 1.2 | 2.1 | 4.0 |
| 5 | 1.5 | 1.8 | 4.2 |
| 6 | 1.3 | 2.0 | 4.2 |
| | 1.2 | 2.0 | 4.5 |
| 7 | 1.3 | 2.1 | 3.5 |
| | 1.35 | 2.5 | 3.7 |
| | 1.1 | 1.7 | 4.0 |
| | 1.2 | 2.0 | 3.5 |
| | 1.4 | | 4.2 |
| | 1.4 | | 4.0 |

| Coefficient of Variation | Number | x + S.D. | C.V. |
|---|---|---|---|
| A | 20 | 1.32 ± .11 | 8.41% |
| B | 18 | 2.1 ± .27 | 13% |
| C | 20 | 4.0 ± .4 | 10% |

In view of the foregoing, it is apparent that the assay technique disclosed herein may be used to determine the presence and concentration of any free species of the type which reversibly bind with protein, provided that a complementary substance capable of specific binding with the species and a distinguishable analogue of the species are available. It is a further requirement that the molecular weight of the species and of its analogue be sufficiently low so that it is feasible to provide microcapsule or other membranes which selectively allow diffusion of these substances while preventing passage of high molecular weight materials such as natural proteins. Fortunately, steroid hormones, thyroid hormones, and other classes of substances of clinical importance are characterized by molecular dimensions far smaller than natural proteins.

The invention may be embodied in other specific forms without departing from the spirit or essential characteristics thereof. The present embodiments and example are therefore to be considered in all aspects as illustrative and not restrictive and the scope of the invention is indicated by the appended claims rather than the foregoing description. All changes which come within the meaning and range of equivalency of the claims are therefore intended to be embraced therein.

We claim:

1. A process for determining in a protein-containing sample the presence of an unbound species capable of reversibly binding to protein, said process comprising the steps of:
   incubating the sample with an antibody complementary to said species and a distinguishable analogue of said species, the sample and antibody being separated by at least one membrane having a porosity sufficient to allow travese of said species and its distinguishable analogue, but insufficient to allow passage of said antibody or protein-bound species,
   allowing unbound species in the sample to traverse said membrane and to compete with its distinguishable analogue for binding sites on said antibody;
   separating said antibody from unbound species and unbound analogue; and
   determine the amount of said distinguishable analogue which is bound to said antibody or which is antibody free, said amount being indicative of the amount of species unbound to protein in the sample.

2. The process of claim 1 wherein
   said antibody and distinguishable analogue are contained within microcapsules comprising said membranes,
   said separation step is effected by removing unbound species and said analogue from said microcapsules and separating said microcapsules from the remainder of the reaction system, and
   the amount of said analogue which is bound to said antibody is determined.

3. The process of claim 1 wherein said distinguishable analogue comprises said species tagged with a radioactive atom.

4. The process of claim 1 or 2 or 3 wherein said species is L-thyroxine.

5. The process of claim 1 or 2 wherein said species is L-3,5,3' tri-iodothyronine.

6. The process of claim 1 or 2 or 3 wherein said species is selected from the group consisting of cortisol, testosterone, and neonatal thyroxine.

7. The process of claim 2 wherein said separating step is effected by inducing an osmolality change in the reaction system which collapses the microcapsules.

8. A test set for use in determining in a liquid sample the amount of an unbound species, said species being capable of reversibly binding with protein in the sample, said test set comprising a mercantile unit comprising in combination:
   a plurality of microcapsules in a container, said microcapsules containing antibody complementary to said species, said microcapsules comprising membranes of a permeability sufficient to allow passage of said species and its distinguishable analogue but insufficient to allow passage of said antibody or natural proteins, said microcapsules being for absorbing unbound species from said sample;
   a reagent in a container, said reagent being capable of removing free species and its analogue from said microcapsules; and
   a standard in a container, said standard containing a predetermined amount of said species, said standard being for comparison with a sample.

9. The test set of claim 8 wherein said species is thyroxine, said distinguishable analogue is radioactively labeled thyroxine, and said standard comprises aliquots of material containing known quantities of free-thyroxine which, when tested in parallel with the sample, allow the construction of a standard curve.

10. The test set of claim 8 wherein said reagent comprises a member selected from the group consisting of serum albumin and polyethyleneimine.

11. A reagent for use in the determination of unbound species in a liquid sample, said species being capable of antibody formation and of reversibly binding with protein in the sample, said reagent comprising a plurality of microcapsules containing antibody complementary to said species and a distinguishable analogue of said species, said microcapsules comprising membranes of a permeability sufficient to allow passage of said species and its distinguishable analogue but insufficient to allow passage of said antibody and natural proteins.

12. The reagent of claim 11 wherein said antibody is complementary to thyroxine and said distinguishable analogue is radioactively labeled thyroxine.

* * * * *

UNITED STATES PATENT AND TRADEMARK OFFICE
CERTIFICATE OF CORRECTION

PATENT NO. : 4,311,690

DATED : January 19, 1982

INVENTOR(S) : Robert J. Buehler, Teresa H. Chan, Franklin Lim

It is certified that error appears in the above-identified patent and that said Letters Patent are hereby corrected as shown below:

Col. 3, line 38, "is" should read --in--.

Col. 10, line 12, "travese" should read --traverse--.

Col. 10, line 20, "determine" should read --determining--.

Col. 10, claim 5, line 1, "1 or 2" should read --1 or 2 or 3--.

Signed and Sealed this

Second Day of November 1982

[SEAL]

Attest:

Attesting Officer

GERALD J. MOSSINGHOFF

Commissioner of Patents and Trademarks